United States Patent
Akash

(10) Patent No.: US 7,517,489 B2
(45) Date of Patent: Apr. 14, 2009

(54) PROCESS FOR MAKING CERAMIC, MINERAL, AND METAL BEADS FROM POWDER

(75) Inventor: Akash Akash, Salt Lake City, UT (US)

(73) Assignee: Ceramatec, Inc., Salt Lake City, UT (US)

( * ) Notice: Subject to any disclaimer, the term of this patent is extended or adjusted under 35 U.S.C. 154(b) by 0 days.

(21) Appl. No.: 11/556,526

(22) Filed: Nov. 3, 2006

(65) Prior Publication Data

US 2007/0104793 A1 May 10, 2007

Related U.S. Application Data

(60) Provisional application No. 60/733,624, filed on Nov. 4, 2005.

(51) Int. Cl.
*B28B 1/00* (2006.01)
*B29B 9/00* (2006.01)
*A61K 9/14* (2006.01)

(52) U.S. Cl. .............. 264/603; 424/489; 264/14

(58) Field of Classification Search ........ 426/426, 426/438; 34/372; 424/489; 264/14, 603
See application file for complete search history.

(56) References Cited

U.S. PATENT DOCUMENTS

| | | | | |
|---|---|---|---|---|
| 3,335,015 A | * | 8/1967 | Forkner | .......... 426/438 |
| 4,124,377 A | * | 11/1978 | Larson | .......... 75/337 |
| 4,441,905 A | | 4/1984 | Malmendier et al. | |
| 5,322,821 A | | 6/1994 | Brezny | |
| 5,384,290 A | | 1/1995 | Brezny | |
| 5,502,012 A | | 3/1996 | Bert et al. | |
| 6,174,466 B1 | * | 1/2001 | Kiefer et al. | .......... 264/4.4 |
| 6,471,894 B1 | * | 10/2002 | Kravchenko et al. | .......... 264/9 |
| 6,596,304 B1 | * | 7/2003 | Bayon et al. | .......... 424/444 |
| 6,761,909 B1 | * | 7/2004 | Etter | .......... 424/489 |
| 6,777,001 B1 | * | 8/2004 | Umezu et al. | .......... 424/489 |
| 6,797,203 B2 | | 9/2004 | Vlach et al. | |
| 7,223,420 B2 | * | 5/2007 | Berger et al. | .......... 424/489 |
| 2006/0184246 A1 | * | 8/2006 | Zwirkoski | .......... 623/11.11 |
| 2008/0299875 A1 | * | 12/2008 | Duescher | .......... 451/56 |

OTHER PUBLICATIONS

Griffin, International Search Report for PCT/US06/43037 sent Sep. 25, 2007, 1-2.
Griffin, Written Opinion for PCT/US06/43037 sent Sep. 25, 2007, 1-5.

* cited by examiner

*Primary Examiner*—Steven P Griffin
*Assistant Examiner*—Russell J Kemmerle, III
(74) *Attorney, Agent, or Firm*—David Fonda

(57) ABSTRACT

A method is provided for synthesizing beads using starting ceramic, metal, or mineral powders. Typical size of these round beads can range from about 0.1 mm to about 10 mm based on the processing variables. In the method, a slip is obtained which contains a metal, ceramic, and/or mineral powder dispersed in a solvent and an organic binder, such as a grain flour. Droplets of the slip are contacted with heated oil for a sufficient time to form beads. The beads are separated from the oil and dried to remove entrained water. The beads are fired at a temperature sufficient to produce beads possessing desired physical or chemical characteristics. The beads have useful biomedical applications as bone filler materials for bone fixation and bone growth. The beads may be coated with chemical catalyst agents and function as catalyst supports in chemical processes.

43 Claims, 1 Drawing Sheet

PROCESS FOR MAKING CERAMIC, MINERAL, AND METAL BEADS FROM POWDER

RELATED APPLICATIONS

This application is related to and claims the benefit of United States Provisional Patent Application Ser. No.: 60/733,624 entitled "PROCESS OF MAKING CERAMIC AND METAL BEADS FROM POWDER" and filed on Nov. 4, 2005 for Akash Akash, which is incorporated herein by reference.

FIELD OF THE INVENTION

The present invention relates to methods for producing generally round ceramic, mineral, or metal beads starting from a ceramic, mineral, or metal powder.

BACKGROUND OF THE INVENTION

Round, roughly spherical beads are used in a wide variety of industrial and medical applications. Their uses range from catalyst supports in chemical processes to bone filler materials in biomedical applications. Typical material systems range from ceramic-based systems like alumina, titania, zirconia, and hydroxyapatite to metals like iron, magnesium, aluminum, copper, and zinc.

In some applications, such as biomedical applications, ceramic granules and beads are used as bone filler materials for bone fixation and bone growth. They have also found wide acceptance in spinal fusion procedures. These synthetic bone substitutes serve to reduce the need for allografts and autografts. In some exemplary procedures, the diameter of the beads used may range from about 0.1 mm to 10 mm.

Currently, such beads are obtained from cadavers and are of irregular shapes. Due to supply limitation and ethical issues there is a need to find synthetic bone substitutes. Commercially available substitutes are mostly available in tubular or elongated shape. It would be an improvement in the art to provide a new source for such products and to increase the range of sizes available along with a method for their manufacture that may render them more affordable to facilitate the provision of appropriate health care to patients.

Such beads and methods and systems for their manufacture are provided herein.

BRIEF SUMMARY OF THE INVENTION

The present invention is directed to ceramic, metal, or mineral beads, methods for their use, and processes, methods, and systems for their production. Beads in a large range of sizes and compositions may be produced using the methods of the present invention. In some embodiments, however, the beads produced have a diameter of from about 0.1 mm to about 10 mm. In others, the beads produced have a diameter of from about 0.1 mm to about 5 mm, and more preferably from about 1 to about 3 mm. In some applications, the beads have a diameter from about 1.7 mm to about 2.4 mm. Such beads are usable as implantable bone substitutes, substrates for bone growth, supports such as catalyst supports, etc. In addition, processes, methods, and systems of the present invention utilize commonly-available organic resources, potentially simplifying production of the beads.

The beads may be prepared by contacting droplets of a metal, ceramic, or mineral slip with hot oil, recovering the beads from the oil, and firing the beads at sufficient temperature to produce beads possessing desired physical or chemical characteristics. The slip is prepared by selecting a suitable starting powder, such as a metal, ceramic, or mineral powder. Examples of typical metal powders include, but are not limited to, aluminum, copper, zinc, lead, and mixtures thereof. Examples of typical ceramic powders include, but are not limited to, titania, zirconia, yttria, alumina, hydroxyapatite, tricalcium phosphate, calcium sulfate, bioglass, magnesia, calcia, spine, chromia, perovskites, silicon carbide, silicon nitride, titanium carbide, boron carbide, boron nitride, silica, and mixtures thereof. Examples of typical mineral powders include, but are not limited to, corundum, aluminosilicate, bauxite, feldspar, mica, and mixtures thereof.

The powder is dispersed in a solvent, such as water, alcohol, or a mixture of water and alcohol, typically at a powder to solvent volume percent ranging from about 10 to about 60 vol. %, and more preferably from about 20 to about 25 vol. %. A dispersant may optionally be added to lower viscosity of the slip. The powder size may range from 10 nm (0.01 microns) to 500 microns, and preferably between 0.1 micron to 200 microns.

An organic binder is added, typically at a ratio of organic binder to powder in the range from about 1:1 to about 1:10, and more preferably in the range from about 1:3 to about 1:5. It has been found that one or more grain flours may function as an organic binder. Examples of suitable grain flours include, but are not limited to, grain flour produced from wheat, rice, chickpeas, and lentils.

Droplets of the slip are contacted with heated oil for a sufficient time to form beads. This step is comparable to cooking, frying or deep frying the droplets. The droplets may typically have a size in the range from about 0.1 mm in diameter to about 10 mm in diameter. Preferably, the droplets have a size in the range from about 0.1 mm in diameter to about 5 mm in diameter, and more preferably from about 1 mm in diameter to about 3 mm in diameter. In some applications, the droplets have a size in the range from about 1.7 mm in diameter to about 2.4 mm in diameter. The heated oil may typically have an oil temperature in the range from about 80° C. to about 150° C. Preferably, the heated oil has an oil temperature in the range from about 90° C. to about 130° C., and more preferably the heated oil has an oil temperature in the range from about 95° C. to about 115° C. The oil may be a common vegetable cooking oil, such as oil derived from canola, corn, olive, peanut, sunflower, or mixtures thereof.

The beads are removed or separated from the oil. To reduce the tendency of the beads from sticking together or agglomerating, it may be desirable to remove oil from the surface of the beads by rinsing the beads with alcohol or acetone. The beads are preferably dried to remove any residual water. The beads may be dried according to any convenient process, including but not limited to, drying at room temperature and drying at higher temperatures. The beads are then fired at a temperature sufficient to produce beads possessing desired physical or chemical characteristics. The firing temperature will typically be in the range of 600° C. to about 2200° C., and more often in the range from 800° C. to about 1400° C. The drying and firing steps may be combined in a single step in which the heating/firing temperature is raised from a low temperature, suitable for drying, to a high temperature, suitable for firing the beads. The resulting beads may be screened or separated according to size.

These and other features and advantages of the present invention will become more fully apparent from the following figures, description, and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE INVENTION

Figure 1:
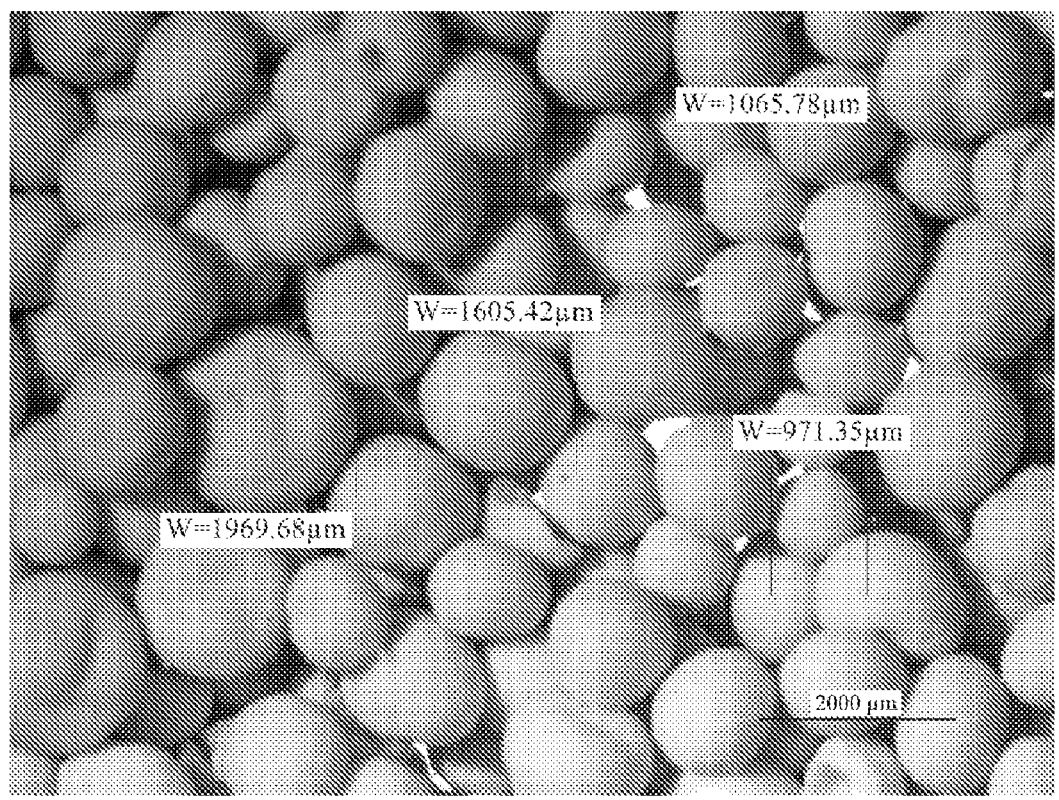
FIG. 1 is a photograph of exemplary hydroxyapatite beads in a range of particle sizes produced from fine powders using methods within the scope of the present invention.

The following more detailed description of the embodiments of the processes, methods, and systems for preparing ceramic, metal, or mineral rounded beads of the present invention, as represented in FIG. 1, is not intended to limit the scope of the invention, as claimed, but is merely representative of a presently preferred embodiment of the invention.

In a first embodiment of the processes of the present invention, a process for making rounded beads from a powder initial ingredient is disclosed. The present invention may be used to produce beads having a very wide variety of chemical compositions, including, but not limited to, ceramic beads produced of any of the common ceramic powders known to one of ordinary skill in the art, metal beads produced from metal powders known to one of ordinary skill in the art, glass beads produced from glass powders known to one of ordinary skill in the art, mineral beads produced from mineral powders known to one of ordinary skill in the art, and beads produced of mixtures of any or all such powders in any ratio. Such metal powders can be but not limited to iron, aluminum, copper, zinc, lead, or mixtures thereof. Such ceramic powders can be but not limited to titania, zirconia, yttria, alumina, hydroxyapatite, tricalcium phosphate, calcium sulfate, bioglass, magnesia, calcia, spinel, chromia, perovskites, silicon carbide, silicon nitride, titanium carbide, boron carbide, boron nitride, silica, or mixtures thereof. Such minerals may be, but not limited to, corundum, aluminosilicate, bauxite, feldspar, mica, or mixtures thereof. The powder size may range from 10 nm (0.01 microns) to 500 microns, and preferably between 0.1 micron to 200 microns.

Mixtures of different powders may be used to produce beads having two or more distinct phases. For example, bioactive powders, such as hydroxyapatite, tricalcium phosphate, calcium sulfate, bioglass may be mixed with bioinert powders such as to titania, zirconia, alumina, etc. to produce a bead having bioactive and bioinert phases.

In this process, the initial powder (which may be ceramic, metal, mineral, or mixtures of two or more powders) is mixed with a solvent, such as water, alcohol, or a water/alcohol mixture, to form a suspension. A variety of different alcohols may be used. It is presently preferred to use lower alkyl alcohols, including by not limited to, methanol, ethanol, isopropanol, butanol, and octanol. In some instances, the volume of solvent to powder ratio is from about 2 to about 90 vol. %. In others, the volume of solvent to powder ratio is from about 10 to about 60 vol. %. In still others, the volume of solvent to powder ratio is from about 20 to about 25 vol. %. A suitable dispersant may be added if a lower viscosity suspension is desired. Such dispersants include, without limitation, Darvan®, poly(methyl methacrylate) (PMMA), glycerol, or polyvinyl alcohol (PVA). Other suitable dispersants will be known to one of ordinary skill in the art.

Following this initial step, an organic binder is added to the suspension to form a slip. In some embodiments, a carbohydrate material is added as the binder. Other suitable binder compositions that produce a bead in a hot oil bath are encompassed within the scope of the present invention and would be known to one of ordinary skill in the art. In some specific embodiments, the binder may be flour. In such embodiments, the flour is generally an organic flour product which is added to the suspension and mixed vigorously until a homogeneous mixture is obtained. In embodiments of the invention, the flour used may be made from crushed and ground wheat, rice, chickpeas, lentil or other grains. The flour could be single component or a mixture of two or more types of flour. The flour to powder weight ratio can vary widely within the scope of the invention such that either a very small or a very large amount is present. In some instances, the flour to powder weight ratio may be from about 1:1 to about 1:10. In other instances, the flour to powder weight ratio may be from about 1:3 to about 1:5.

The amount of binder added to the suspension will affect the porosity of the resulting bead. A larger quantity of binder will result in a more porous or less dense bead. The amount of binder also affects the viscosity of the suspension or slip formed from the powder. It is more difficult to form round droplets from a viscous suspension. In addition, more binder present in the composition enables larger beads to be formed.

Following production of the slip, the slip is formed into small droplets using any of a number of technologies available in the art. In one embodiment, the slip may be dispensed from a small orifice of a device in the form of small droplets. One such suitable device could be a syringe or a mechanical or pressure controlled device that allows for controlled delivery of the slip through one or more small orifice. The device can be automated, scaled, and controlled to provide various quantities and sizes of droplets. The device may also produce a fine mist or spray of the slip. Other suitable devices will be known to one of ordinary skill in the art.

As discussed briefly above, the droplet size may be widely varied within the scope of the invention. In some instances, the droplet size may range from about 0.1 mm in diameter to about 10 mm in diameter. Preferably, the droplets may have a size in the range from about 0.1 mm in diameter to about 5 mm in diameter, and more preferably from about 1 mm in diameter to about 3 mm in diameter. In some embodiments, the droplets have a size in the range from about 1.7 mm in diameter to about 2.4 mm in diameter. Very small droplet sizes are possible if the slip is sprayed.

The droplets are placed or dropped into a heated oil bath having a temperature sufficient to cook or burn out the binder (organic) component of the beads. In some instances, this temperature may be from about 80° C. to about 150° C. A more preferred temperature may be from about 90° C. to about 130° C., and more preferably from about 95° C. to about 115° C. The oil used in the bath may be varied widely within the scope of the invention as well. In some instances, the oil used in the bath may be a common vegetable cooking oil such as, but not limited to, any of the cooking oils used in the food industry such as, without limitation, canola, corn, olive, peanut, sunflower, or any mixture of the above.

Beads are immediately formed by hardening when the droplets come into contact with the heated oil. After exposing the beads to the heated oil for at least a few seconds, but more typically from about 1 to 5 minutes, the beads may be removed from the oil bath using any suitable process, such as, but not limited to, straining or filtering. The required cooking time may vary depending upon the size of the beads. Larger beads will require longer exposure time to the oil than smaller, finer beads. Usually, excess cooking time will not harm the formed beads.

The beads may optionally be rinsed in an alcohol or acetone medium to remove remaining oil from the surface. This helps prevent the beads from agglomerating or sticking together. Typical alcohols that may be used include, without limitation, methanol, ethanol, isopropanol, butanol, etc. The beads, which in some instances may be produced to range from 0.1 mm to 10 mm in diameter, are sometimes larger than the initial droplet size.

The beads are preferably dried to remove any solvent remaining within the bead. A variety of processes may be used to dry the beads, including, but not limited to, drying at room temperature and drying at higher temperatures. For example, the beads may be baked at a temperature below 100° C. for several hours, such as overnight. A lower temperature from about 50° C. to about 70° C. may be used. An optional second baking step, at a temperature greater than 100° C., may further help remove solvent from the beads. In this manner, solvent may be removed in stages. It is currently preferred to remove solvent, particularly water, from the beads prior to firing the beads at very high temperatures. Residual water in the beads can damage the beads when they are fired.

Following this drying step, the beads may be fired at a desired temperature to obtain the required strength, porosity and chemical phase. Firing temperatures and times may vary within the scope of the invention. For example, typical firing temperatures range from about 600° C. to about 2200° C. For many beads, the firing temperature will range from about 800° C. to about 1400° C., and more preferably from about 1200° C. to about 1300° C. Those of ordinary skill in the art will appreciate that the firing temperature may be adjusted to produce beads possessing desired physical characteristics and properties. The firing temperature is also affected by the choice of powder material used to form the slip. During firing, the binder material substantially burns off, leaving the powder material fused together. In some cases, the drying and firing steps may be performed in a single step in which the heating/firing temperature is raised from a low temperature, suitable for drying, to a high temperature, suitable for firing the beads. The resulting beads may be sorted by size using conventional screening techniques.

EXAMPLE 1

In a first example, hydroxyapatite powder was mixed with water in the ratio of from about 20 to about 25 vol. % powder to water. A chickpea flour was added to the suspension in the weight ratio of about 1:5. The mixed suspension was then added dropwise through a syringe into a pan of heated olive oil at 115° C. The beads were formed in the range of from about 1 mm to about 5 mm depending on the starting droplet size. The beads were separated using a strainer and rinsed in methanol or acetone to remove the excess oil from the bead. The beads were then dried at about 40° C. and fired to about 1300° C. to get dense, strong hydroxyapatite beads. FIG. 1 includes a photograph of beads prepared according to this method.

Load bearing tests were performed on the beads. The beads were inserted into a 3.2 mm (inner diameter) hollow steel tube up to a height less than 2 cm. A 700N load was applied at 60 Hz cycle for approximately 1 million cycles. After the loading test, the beads exhibited greater than 90% height retention (control samples had a height retention of ~86%) and minimal fracturing or cracking.

EXAMPLE 2

Titanium metal powder is mixed with water in the ratio of from about 25 to about 30 vol. % powder to water. A chickpea flour is added to the suspension in the weight ratio of about 1:5. The mixed suspension is then added dropwise through a syringe into a pan of heated olive oil at 115° C. The beads are formed in the range of from about 2 mm to about 3 mm depending on the starting droplet size. The beads are separated using a strainer and rinsed in methanol or acetone to remove the excess oil from the bead. The beads are then dried at about 70° C. to remove water, and then fired to about 1100° C. to get strong titanium metal beads.

EXAMPLE 3

Aluminum oxide powder is mixed with water in the ratio of from about 20 vol. % powder to water. A chickpea flour is added to the suspension in the weight ratio of about 1:5. The mixed suspension is then added dropwise through a syringe into a pan of heated olive oil at 115° C. The beads are formed in the range of from about 2 mm to about 3 mm depending on the starting droplet size. The beads are separated using a strainer and rinsed in methanol or acetone to remove the excess oil from the bead. The beads are then dried at about 70° C. to remove water, and then fired to about 1600° C. to get dense, strong alumina beads.

EXAMPLE 4

Two different types of calcium phosphate-based powders are mixed together in dry form. The individual powders in dry form—hydroxyapatite (65 wt. %) and tricalcium phosphate (35 wt. %)—are mixed together in a bottle. Next, water is added in the ratio of about 20 vol. % powder to water. A chickpea flour is added to the suspension in the weight ratio of about 1:5. The mixed suspension is then added dropwise through a syringe into a pan of heated olive oil at 115° C. The beads are formed in the range of from about 2 mm to about 3 mm depending on the starting droplet size. The beads are separated using a strainer and rinsed in methanol or acetone to remove the excess oil from the bead. The beads are then dried at about 50° C. and fired to about 1300° C. to obtain bioceramic beads with two phases (hydroxyapatite and tricalcium phosphate).

EXAMPLE 5

Hydroxyapatite powder is mixed with water in the ratio of about 20 vol. % powder to water. A chickpea flour is added to the suspension in the weight ratio of about 1:3. A lower ratio of chickpea flour results in a lower viscosity of the final suspension. The mixed suspension is then added dropwise through a syringe into a pan of heated olive oil at 115° C. The beads are formed in the range of from about 1 mm to about 2 mm depending on the starting droplet size. A smaller bead size is obtained in this case due to the lower starting viscosity which in turn leads to a smaller starting droplet size. The beads are separated using a strainer and rinsed in methanol or acetone to remove the excess oil from the bead. The beads are then dried at about 40° C. and fired to about 1300° C. to get dense, strong hydroxyapatite beads.

Beads prepared according to methods within the scope of the present invention may be used in many different applications. In some applications, such as biomedical applications, ceramic granules and beads may be used as bone filler materials for bone fixation and bone growth. They may be used in spinal fusion procedures. The choice of starting powder may be varied depending on the desired end use. For example, the powder or mixture of powders may vary depending upon whether the beads are used for bone replacement or bone repair procedures. Such powders may include hydroxyapatite, tricalcium phosphate, calcium sulfate, bioglass, or mixtures thereof.

Because the beads are porous, the beads may be infiltrated with bioactive substances including, but not limited to, anti-inflammatory agents, bone growth factors, antibiotic agents, bactericidal agents or other desirable bioactive substances. The beads may be coated with chemical catalyst agents and thereby function as catalyst supports in chemical processes. Because the choice of starting powder may vary, the methods within the scope of the present invention may prepare different beads tailored to specific applications.

While specific embodiments of the present invention have been illustrated and described, numerous modifications come to mind without significantly departing from the spirit of the invention, and are included within its scope.

The invention claimed is:

1. A method of preparing beads comprising:
   obtaining a slip comprising a quantity of powder, a solvent, and an organic binder, wherein the powder is selected from metal powders, ceramic powders, mineral powders, and mixtures thereof;
   forming one or more droplets of the slip;
   introducing one or more of the droplets into a heated oil bath for a sufficient time to form one or more beads;
   separating the beads from the oil; and
   firing the beads at a temperature sufficient to produce beads possessing desired physical or chemical characteristics.

2. The method of preparing beads according to claim 1, wherein the droplets have a size in the range from about 0.1 mm in diameter to about 10 mm in diameter.

3. The method of preparing beads according to claim 1, wherein the droplets have a size in the range from about 0.1 mm in diameter to about 5 mm in diameter.

4. The method of preparing beads according to claim 1, wherein the droplets have a size in the range from about 1 mm in diameter to about 3 mm in diameter.

5. The method of preparing beads according to claim 1, wherein the droplets have a size in the range from about 1.7 mm in diameter to about 2.4 mm in diameter.

6. The method of preparing beads according to claim 1, wherein the heated oil bath has an oil temperature in the range from about 80° C. to about 150° C.

7. The method of preparing beads according to claim 1, wherein the heated oil bath has an oil temperature in the range from about 90° C. to about 130° C.

8. The method of preparing beads according to claim 1, wherein the heated oil bath has an oil temperature in the range from about 95° C. to about 115° C.

9. The method of preparing beads according to claim 1, wherein the powder size ranges from 10 nm (0.01 microns) to 500 microns.

10. The method of preparing beads according to claim 1, wherein the powder size ranges from 0.1 micron to 200 microns.

11. The method of preparing beads according to claim 1, wherein the powder comprises a metal powder selected from iron, aluminum, copper, zinc, lead, and mixtures thereof.

12. The method of preparing beads according to claim 1, wherein the powder comprises a ceramic powder selected from hydroxyapatite, tricalcium phosphate, calcium sulfate, bioglass, titania, zirconia, yttria, alumina, magnesia, calcia, spinel, chromia, perovskites, silicon carbide, silicon nitride, titanium carbide, boron carbide, boron nitride, silica, and mixtures thereof.

13. The method of preparing beads according to claim 1, wherein the powder comprises a mixture of powders comprising at least one bioactive ceramic powder selected from hydroxyapatite, tricalcium phosphate, calcium sulfate, bioglass and at least one bioinert ceramic powder selected from titania, zirconia, yttria, alumina, magnesia, calcia, spinel, chromia, perovskites, silicon carbide, silicon nitride, titanium carbide, boron carbide, boron nitride, silica.

14. The method of preparing beads according to claim 1, wherein the powder comprises a mineral powder selected from corundum, aluminosilicate, bauxite, feldspar, mica, and mixtures thereof.

15. The method of preparing beads according to claim 1, wherein the powder comprises hydroxyapatite.

16. The method of preparing beads according to claim 15, wherein the powder further comprises tricalcium phosphate, calcium sulfate or bioglass.

17. The method of preparing beads according to claim 1, wherein the volume of powder to solvent ratio is from about 10 to about 60 vol. %.

18. The method of preparing beads according to claim 1, wherein the volume of powder to solvent ratio is from about 20 to about 25 vol. %.

19. The method of preparing beads according to claim 1, wherein the solvent is selected from water, alcohol, or a mixture of water and alcohol.

20. The method of preparing beads according to claim 1, further comprising a dispersant to lower viscosity of the slip.

21. The method of preparing beads according to claim 1, wherein the organic binder comprises one or more grain flours.

22. The method of preparing beads according to claim 21, wherein the one or more grain flours are produced from grains selected from wheat, rice, chickpeas, and lentils.

23. The method of preparing beads according to claim 1, wherein the ratio of organic binder to powder is in the range from about 1:1 to about 1:10.

24. The method of preparing beads according to claim 1, wherein the ratio of organic binder to powder is in the range from about 1:3 to about 1:5.

25. The method of preparing beads according to claim 1, wherein the powder is selected from hydroxyapatite, tricalcium phosphate, calcium sulfate, bioglass or mixtures thereof, the volume of powder to water ratio is from about 20 to about 25 vol. %, the binder comprises chickpea flour, and the ratio of organic binder to powder is in the range from about 1:3 to about 1:5.

26. The method of preparing beads according to claim 1, wherein the oil is a vegetable cooking oil.

27. The method of preparing beads according to claim 1, wherein the oil is a vegetable cooking oil selected from oil derived from canola, corn, olive, peanut, sunflower, or mixtures thereof.

28. The method of preparing beads according to claim 1, further comprising the step of removing oil from the surface of the beads.

29. The method of preparing beads according to claim 28, wherein oil is removed from the surface of the beads by rinsing the beads in an alcohol or acetone medium.

30. The method of preparing beads according to claim 1, further comprising the step of separating the beads according to size.

31. The method of preparing beads according to claim 1, further comprising the step of drying the beads to remove entrained solvent.

32. The method of preparing beads according to claim 31, wherein the drying step and firing step are combined such that the beads are initially heated at a drying temperature and then fired at a firing temperature.

33. The method of preparing beads according to claim 1, wherein the beads are fired at a temperature in the range from about 600° C. to about 2200° C.

34. The method of preparing beads according to claim 1, wherein the beads are fired at a temperature in the range from about 800° C. to about 1400° C.

35. The method of preparing beads according to claim 1, further comprising the step of infiltrating the beads with a bioactive substance selected from anti-inflammatory agents, bactericidal agents, bone growth factors, and antibiotic agents.

36. The method of preparing beads according to claim 1, further comprising the step of coating the beads with chemical catalyst agent.

37. A method of preparing ceramic beads comprising:
obtaining a slip comprising a quantity of powder selected from hydroxyapatite, tricalcium phosphate, calcium sulfate, bioglass, and mixtures thereof, a solvent, and one or more grain flours, wherein the powder has a particle size ranging from 10 nm to 500 microns;
forming droplets of the slip having a droplet size in the range from about 0.1 mm in diameter to about 10 mm in diameter;
contacting the droplets with a heated oil bath for a sufficient time to form beads;
separating the beads from the oil;
removing oil from the surface of the beads;
drying the beads to remove entrained solvent; and
firing the beads at a temperature sufficient to produce ceramic beads possessing desired physical or chemical characteristics.

38. A method of preparing beads comprising:
obtaining a slip comprising a quantity of powder, a solvent, and an organic binder, wherein the powder is selected from metal powders, ceramic powders, mineral powders, and mixtures thereof;
forming droplets of the slip;
contacting the droplets with heated oil for a sufficient time to form beads, said heated oil having a temperature of at least 95° Celsius;
separating the beads from the oil; and
firing the beads at a temperature sufficient to produce beads possessing desired physical or chemical characteristics.

39. The method of preparing beads according to claim 38, wherein the organic binder comprises at least one grains selected from wheat, rice, chickpeas, lentils and combinations thereof.

40. A method of preparing beads comprising:
obtaining a slip comprising a quantity of powder, a solvent, and an organic insoluble binder, wherein the powder is selected from metal powders, ceramic powders, mineral powders, and mixtures thereof;
forming droplets of the slip;
evaporating at least a portion of the solvent by contacting the droplets with heated oil for a sufficient time to form beads;
separating the beads from the oil; and
firing the beads at a temperature sufficient to produce beads possessing desired physical or chemical characteristics.

41. The method of preparing beads according to claim 40, wherein the organic binder comprises at least one grains selected from wheat, rice, chickpeas, lentils and combinations thereof.

42. A method of preparing beads comprising:
obtaining a slip comprising a quantity of powder having a mean diameter of greater than 100 microns, a solvent, and an organic insoluble binder, wherein the powder is selected from metal powders, ceramic powders, mineral powders, and mixtures thereof;
forming droplets of the slip;
contacting the droplets with heated oil for a sufficient time to form beads;
separating the beads from the oil; and
firing the beads at a temperature sufficient to produce beads possessing desired physical or chemical characteristics.

43. The method of preparing beads according to claim 42, wherein the organic binder comprises at least one grains selected from wheat, rice, chickpeas, lentils and combinations thereof.

* * * * *